United States Patent [19]

Saito

[11] Patent Number: 5,200,148
[45] Date of Patent: Apr. 6, 1993

[54] CHEMICAL ASSAY TAPE

[75] Inventor: Yoshio Saito, Saitama, Japan

[73] Assignee: Fuji Photo Film Co., Ltd., Kanagawa, Japan

[21] Appl. No.: 692,969

[22] Filed: Apr. 29, 1991

Related U.S. Application Data

[63] Continuation of Ser. No. 288,883, Dec. 23, 1988, abandoned.

[30] Foreign Application Priority Data

Jan. 11, 1988 [JP] Japan .................... 63-3448

[51] Int. Cl.$^5$ ............................. G01N 31/22
[52] U.S. Cl. .......................... 422/56; 422/66
[58] Field of Search ............... 422/55, 56, 57, 66; 435/805

[56] References Cited

U.S. PATENT DOCUMENTS

| | | | |
|---|---|---|---|
| 3,260,413 | 7/1966 | Natelson | 422/66 X |
| 3,526,480 | 9/1970 | Findl et al. | 422/66 |
| 3,992,158 | 11/1976 | Przybylowicz et al. | 422/57 |
| 4,071,315 | 1/1978 | Chateau | 422/66 X |
| 4,087,332 | 5/1978 | Hansen | 435/805 X |
| 4,218,421 | 8/1980 | Mack, Jr. et al. | 422/66 |
| 4,250,257 | 2/1981 | Lee et al. | 422/66 X |
| 4,292,272 | 9/1981 | Kitajima et al. | 422/57 |
| 4,526,823 | 7/1985 | Farrell et al. | |
| 4,595,439 | 7/1986 | Boger et al. | 422/57 |
| 4,837,373 | 6/1989 | Gunkel et al. | 422/57 X |
| 5,075,077 | 12/1991 | Durley et al. | 422/56 |
| 5,077,010 | 12/1991 | Ishizaka et al. | 422/56 |

FOREIGN PATENT DOCUMENTS

| | | |
|---|---|---|
| 2151713 | 4/1973 | France . |
| 0101760 | 4/1982 | Japan . |
| 0101761 | 6/1982 | Japan . |
| 0066359 | 9/1982 | Japan . |
| 0193352 | 3/1984 | Japan . |
| 0102388 | 12/1984 | Japan . |

*Primary Examiner*—James C. Housel
*Assistant Examiner*—Jeffrey R. Snay
*Attorney, Agent, or Firm*—Sughrue, Mion, Zinn, Macpeak & Seas

[57] ABSTRACT

A chemical assay tape including a water-impermeable support and at least one water-permeable layer. The water-permeable layer includes at least one porous layer for allowing a liquid applied thereto to spread out. At least one layer other than the support is provided with a plurality of grooves which are spaced at constant intervals and extend across the chemical assay tape.

7 Claims, 1 Drawing Sheet

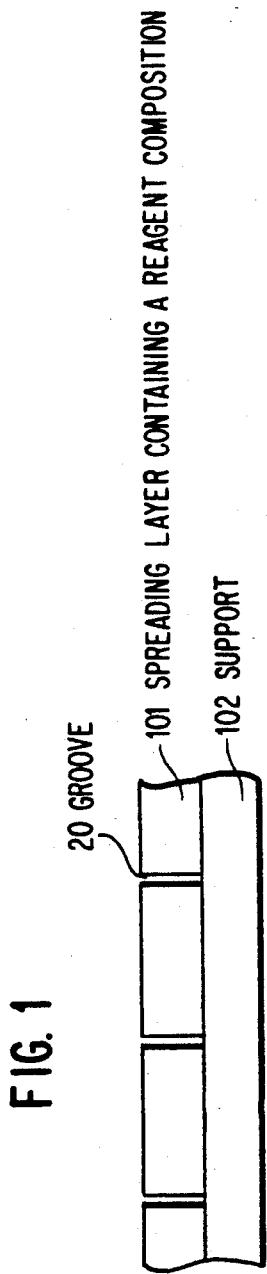
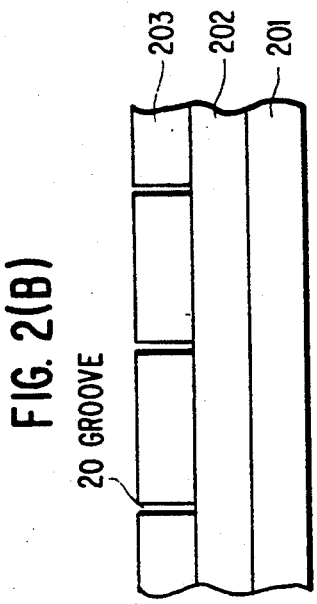
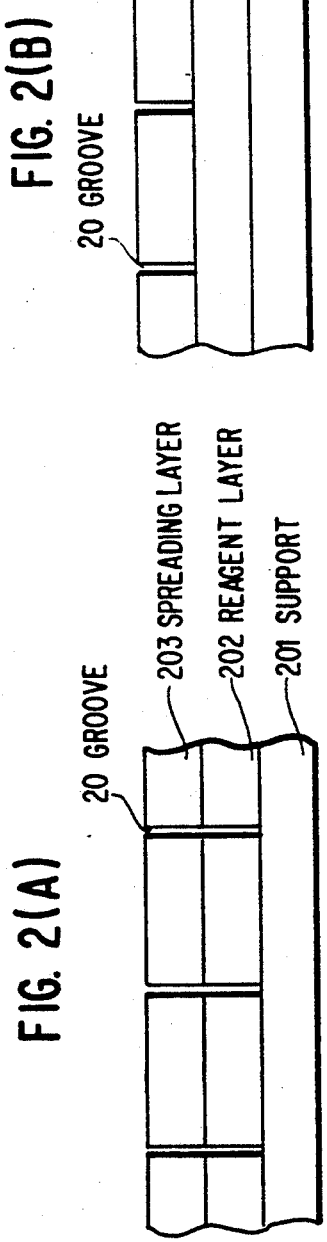
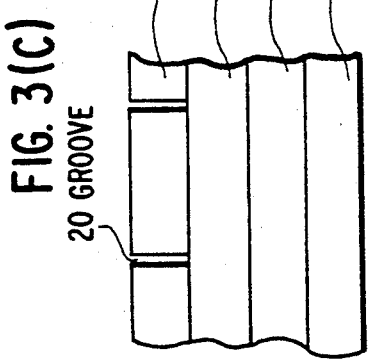
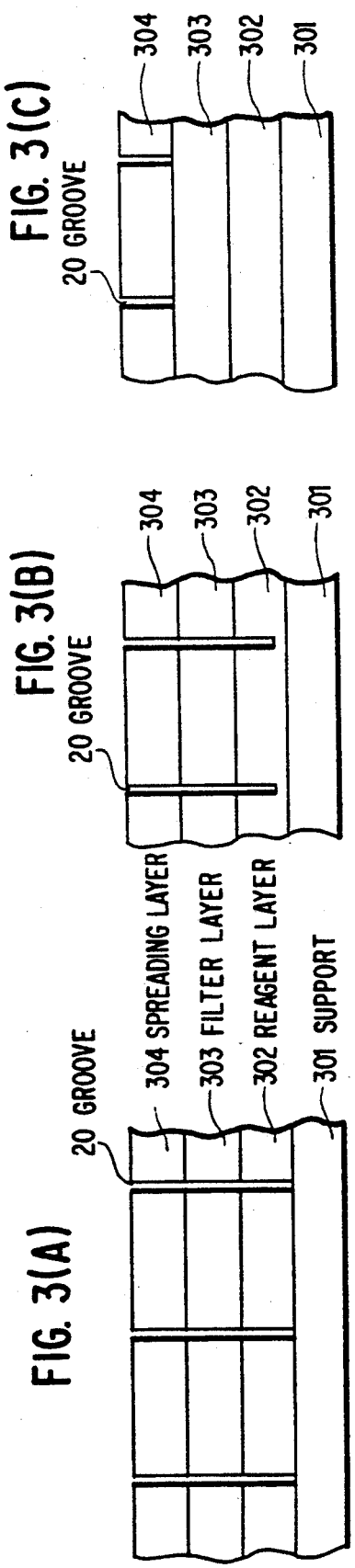

CHEMICAL ASSAY TAPE

This is a continuation of application Ser. No. 07/288,883 filed Dec. 23, 1988, now abandoned.

BACKGROUND OF THE INVENTION

1. Field of the Invention

This invention relates to a chemical assay tape for determining the quantity of a specific substance in a body fluid (e.g. blood, serum, urine, etc) of an organism or the like.

2. Description of the Prior Art

Determination of the amounts of various metabolites in body fluids, e.g. glucose, bilirubin, urea, uric acid, cholesterol, lactic dehydrogenase, creatine kinase, GOT, GPT, etc, is clinically important and essential to the diagnosis of diseases, follow-up studies of medical treatments, prognoses and the like. In a clinical chemical test in which blood or the like is used as a sample, it is desirable to conduct a highly accurate test by using a very small quantity of a liquid sample. Although a so-called wet method employing a solution reagent has been used widely, tests using this method cannot be conducted as quickly as would be desirable.

As a means for quickly conducting a highly accurate test by using a very small quantity of a liquid sample, chemical assay slides have been developed by utilizing dry-type multilayer films. There are various types of the chemical assay slides according to their layer structures.

An example of types of assay slide is a dry-type, multilayered film sandwiched between a pair of plastic frames. An opening into which a liquid sample may be deposited is formed in the center of the upper frame, while an opening through which optical measurements can be made is formed in the lower frame. The multilayered films are composed of a transparent support, a reagent layer, a reflection layer, and a spreading layer. The transparent support is, for example, a subbed, thin plastic film. The reagent layer, coated on the transparent support contains a reagent which reacts with a substance contained in a liquid sample, and after the reaction, the reagent layer exhibits an optical density, the value of which depends on quantity of the substance which was originally contained in the sample. The reflection layer prevents the light incident on the reagent layer from reaching the spreading layer, so that the liquid sample supplied to the spreading layer is not optically detected. In the spreading layer, the deposited liquid sample uniformly spreads over an area which is substantially proportional to the quantity of the deposited liquid sample.

In order to determine the amount of a substance contained in a liquid sample by using such a chemical assay slide, a predetermined amount of the liquid sample, e.g. whole blood, is spotted onto the surface of the spreading layer through the opening of the upper frame. The blood spreads into the spreading layer and passes through the reflection layer to reach the reagent layer where it reacts with the reagent to form a product having a specific color, hereinafter sometimes called a colorant. After the deposition of the liquid sample, the chemical assay slide is maintained at a constant temperature for an appropriate period of time so that the color reaction, i.e. the reaction forming a product having a specific color, advances sufficiently. Then, the reagent layer is illuminated with light through the opening in the lower frame. The amount of reflected light in a predetermined region of wavelength is measured so as to determine the optical density of reflection. The amount of the substance in question is determined on the basis of a curve indicating known optical density versus sample component quantity which was obtained prior to the deposition of the sample liquid.

Such a chemical assay slide can be prepared for each substance which is to be subjected to assay, but this may lead to rather disadvantage in view of the expense involved. Firstly, the process for manufacturing chemical assay slides may be laborious. In order to mass-produce the chemical assay slides, a sheet of film having a large area is made and then cut into small pieces. Thereafter, each piece is fixed to a frame so that a chemical assay slide is formed. It may be particularly laborious to cut out film pieces having a precise size and to fix them accurately to the frame. Although the manual labor required can be reduced by using an automatic machine, considerable investment and maintenance are required therefor. Secondly, the material for the frame and the processing thereof for finishing the slide may be costly.

By configuring the chemical assay film as a long tape, the labor and cost required to produce a slide for each sample can be eliminated.

Chemical assay tapes are mentioned, in combination with analysis apparatuses, in U.S. Pat. No. 3,260,413, U.S. Pat. No. 3,526,480, and U.S. Pat. No. 3,992,158. However, as stated in U.S. Pat. No. 3,992,158, the analysis apparatuses disclosed in U.S. Pat. No. 3,260,413 and U.S. Pat. No. 3,526,480 have a complicated structure in which two or more tapes are temporarily brought into contact with each other to form a composite and then separated from each other. U.S. Pat. No. 3,992,158 states that the chemical assay tapes in accordance with that patent are advantageous in that a complicated apparatus is unnecessary and that assay tapes of different types can be used simultaneously or successively.

However, when the integral multilayered assay tape disclosed in U.S. Pat. No. 3,992,158 is formed as a long tape and wound up in a roll so that the tape can be received in a container or continuously supplied to an analysis apparatus, the spreading layer, which is composed of a non-fibrous porous medium, often cracks.

The multilayered assay film disclosed in U.S. Pat. No. 4,292,272 has a spreading layer made of a fibrous porous medium. Thus, the spreading layer does not crack easily. However, when a porous layer, e.g. a filter layer, is disposed between the spreading layer and the reagent layer, the porous layer often cracks during the manufacture of the film or the handling of the film for an assay. The cracked portion cannot be used for assay of a liquid sample. For example, during the manufacture, while a multilayered chemical assay film having a porous filter layer between a spreading layer and a reagent layer is dried in vacuum in order to control the moisture content, the filter layer or the like often cracks.

SUMMARY OF THE INVENTION

The object of the present invention is to provide a chemical assay tape, especially one having a long length, in which a layer, a porous layer in particular, is prevented from cracking.

BRIEF DESCRIPTION OF THE DRAWINGS

FIG. 1 is a first layer structure of the present invention;

FIG. 2(a) is a second layer structure of the present invention with grooves through two layers;

FIG. 2(b) is the second layer structure of the present invention with grooves through one layer;

FIG. 3(a) is a third layer structure of the present invention with grooves through three layers;

FIG. 3(b) is the third layer structure of the present invention with grooves through two layers and part of the third layer; and FIG. 3(c) is the third layer structure of the present invention with grooves through one layer.

DETAIL DESCRIPTION OF THE PREFERRED EMBODIMENT

In accordance with the present invention, the above-mentioned object is achieved by forming a plurality of grooves on a layer of a chemical assay tape other than a support layer thereof so that they extend across the chemical assay tape while maintaining a substantially constant space between each adjacent groove 20.

The proper depth of the grooves 20 varies according to the rigidity of the support and other layers as well as the width of the tape.

The grooves 20 may be formed only across the layer which is farthest from the support, or they may be formed across two or more layers. Preferably, a chemical assay tape is provided with the grooves traversing all the layers except for the support as in FIG. 2(a) and FIG. 3(a).

In cases where an assay tape has a polyethylene terephthalate support having a thickness of about 0.2–0.3 mm and a width of about 5–15 mm, and has water-permeable layers of 0.1 to 0.5 mm in total thickness the depth of the grooves is not greater than 0.5 mm, in general.

The interval of the grooves in the longitudinal direction of the tape is preferably less than 50 mm, more preferably at most 30 mm.

The shape of the groove in the transverse section may be U-shape, V-shape, rectangular, or the like.

The chemical assay tape in accordance with the present invention preferably comprises the materials described, for example, in U.S. Pat. 4,292,272, Japanese Unexamined Patent Publication Nos. 59(1984)-102388 and 60(1985)-222769.

When a water-impermeable and light transmissive support is used, the film used for the assay tape in accordance with the present invention may have layer structures as exemplified by the following:

(1) A structure in which a spreading layer 101 containing a reagent composition is mounted on a support 102.

(2) A structure in which a support 201, a reagent layer 202 and a spreading layer 203 are mounted in this order.

(3) A structure in which a support 301, a reagent layer 302, a filter layer 303 and a spreading layer 304 are mounted in this order.

(4) A structure in which a support, an indicator layer, a reagent layer and a spreading layer are mounted in this order.

(5) A structure in which a support, an indicator layer, a filter layer and a spreading layer are mounted in this order.

(6) A structure in which a support, a reagent layer, a light reflection layer and a spreading layer are mounted in this order.

(7) A structure in which a support, a light reflection layer, a filter layer and a spreading layer are mounted in this order.

(8) A structure in which a support, an indicator layer, a reagent layer, a light reflection layer and a spreading layer are mounted in this order.

(9) A structure in which a support, a reagent layer, a light reflection layer, a filter layer and a spreading layer are mounted in this order.

(10) A structure in which a support, an indicator layer, a light reflection layer, a reagent layer and a spreading layer are mounted in this order.

(11) A structure in which a support, an indicator layer, a light reflection layer, a reagent layer, a filter layer and a spreading layer are mounted in this order.

(12) A structure in which a support, a second reagent layer, an anti-interferent layer, a first reagent layer and a spreading layer are mounted in this order.

(13) A structure in which a support, a second reagent layer, an anti-interferent layer, a first reagent layer, a filter layer and a spreading layer are mounted in this order.

A water absorbing layer may be provided between the support and the spreading layer or between the reagent layer and the indicator layer. Also, in the above-mentioned structures (1)–(11), an anti-interferent layer may be provided between the reagent layer and the spreading layer. In the above-mentioned structures (12) and (13), a registration layer may be provided between the support and the second reagent layer, while a light reflection layer or the like may be provided between the second reagent layer and the registration layer. Also, the light reflection layer may be provided somewhere between the second reagent layer, the anti-interferent layer, the first reagent layer, the filter layer and the spreading layer.

The indicator layer is generally defined as a layer in which a colorant or the like, which was generated in the presence of a substance to be determined is diffused and can be detected optically through the light transmissive layer. The registration layer may be made of a hydrophilic polymer. The water absorbing layer is generally defined as a layer into which the colorant or the like, which has been generated in the presence of the substance to be determined cannot be diffused. The water absorbing layer may be made of a hydrophilic polymer which swells easily.

The filter layer, especially one for filtering blood cells, is disclosed, for example, in U.S. Pat. No. 3,992,158, Japanese Unexamined Patent Publication Nos. 62(1987)-138756, -138757 and -138758. The anti-interferent layer is disclosed, for example, in U.S. Pat. No. 4,303,408. The light reflection layer is disclosed, for example, in U.S. Pat. No. 4,042,335. The anti-interferent layer to be disposed between the first and second reagent layers is disclosed, for example, in U.S. Pat. No. 4,066,403.

Preferably, the spreading layer supplies a uniform quantity of the liquid sample per unit area to the adjacent water-permeable layer. The spreading layer used in the chemical assay tape in accordance with the present invention preferably comprises fiber material such as the cloth disclosed in U.S. Pat. No. 4,292,272 or the knitted material disclosed in Japanese Unexamined Patent Publication No. 60(1985)-222769. The cloth or the like may be subjected to glow discharge processing as disclosed in Japanese Unexamined Patent Publication No. 57(1982)-66359. The spreading layer may contain a hydrophilic polymer or a surfactant such as the one disclosed in Japanese Unexamined Patent Publication Nos. 60(1985)-222770, 62(1987)-182652, 63(1988)-112999, and 63(1988)-219393, in order to control the area over which the sample liquid spreads, the speed at which the sample liquid spreads, and the like.

A bonding layer by which the spreading layer is bonded to the adjacent layer may be disposed on a layer such as a reagent layer, a light reflection layer, a filter layer, a water absorbing layer, or a registration layer. In general, the bonding layer comprises a hydrophilic polymer (e.g. gelatin, gelatin derivatives, polyacrylamide, or starch) which adheres to a porous layer, when swelled with water.

The chemical assay tape in accordance with the present invention may have a light reflection layer (which is disposed, for example, between a reagent layer and a registration layer or between a reagent layer and a spreading layer). The light reflection layer masks the color of a sample liquid supplied to the spreading layer (in particular the red color of hemoglobin and the yellow color of bilirubin in cases where whole blood is used as the sample liquid) and functions as a light reflection layer or a background layer when a detectable change (in color or the like) appearing in the registration layer, the reagent layer or the like is measured on the basis of the ratio of light which is transmitted through a light transmissive substrate to the light which is reflected by the light reflection layer. Preferably, the light reflection layer is a water permeable layer in which light reflective fine particles such as titanium oxide or barium sulfate are dispersed by using a hydrophilic polymer as a binder.

The reagent layer or the like of the chemical assay tape in accordance with the present invention contains a composition which can produce a substance which is optically detectable e.g. a dye. For example the reagent layer could contain a composition which produces a dye due to oxidation of leuco dye (e.g. arylimidazole leuco dye as disclosed in U.S. Pat. No. 4,089,747 and Japanese Unexamined Patent Publication No. 59(1984)-(193352), a composition containing compounds, which produce a dye when oxidized (e.g. 4-aminoantipyrin and phenol or naphthol), or a compound which can produce a dye in the presence of a reduction type coenzyme and an electron transferring agent. When a chemical assay film is used for determining the level of an enzymatic activity, a self color-developing substrate such as p-nitrophenol may be contained in the reagent layer, the spreading layer, or the like.

The reagent layer in the chemical assay tape in accordance with the present invention may be a substantially uniform layer containing a hydrophilic polymer as a binder, or it may be a porous layer. All the reagent compositions may be contained in a single layer. Alternatively, a part of them may be contained in another porous or non-porous layer. For example, a composition which reacts with the substance to be determined to form an intermediate product may be contained in the first reagent layer, while a composition (indicator) which reacts with the intermediate product to form a dye or the like may be contained in the second reagent layer which is disposed between the first reagent layer and the support. As the reagent layer, a fibrous porous layer such as filter paper or nonwoven cloth, or a nonfibrous porous layer may be used. Preferably, a blushed polymer layer made of cellulose ester as disclosed in U.S. Pat. No. 1,421,341, U.S. Pat No. 3,992,158 or the like, e.g. cellulose acetate, cellulose acetate/butyrate or cellulose nitrate is used. This layer may be a fine porous membrane made of polyamide such as 6-nylon or 6.6-nylon, polyethylene, polypropyrene or the like. Also, this layer may be a fine porous layer made of polysulfone as disclosed in Japanese Unexamined Patent Publication No. 62(1987)-27006. Further, a porous layer, having a continuous void, in which fine polymer particles, glass particles, diatomaceus earth particles or the like are combined with a hydrophilic or non water-absorptive polymer, as disclosed in U.S. Pat. No. 3,992,158, U.S. Pat. No. 4,258,001 or the like; or a polymer particle structure as disclosed in Japanese Unexamined Patent Publication Nos. 57(1982)-101760, 57(1982)-101761, or the like, may be utilized.

A support which cannot transmit light or is opaque may also be used in the chemical assay tape in accordance with the present invention.

In general, the chemical assay tape in accordance with the present invention is wound up around a core or a reel so as to form a roll. Also, the tape may be wound up within a drum-like container without a core. The core, the reel or the like may be formed by one or more of the usual materials such as wood, metals, thermoplastic polymers or thermosetting resins. Preferably, the diameter of the roll is not smaller than 30 mm. When the thickness of the chemical assay tape is not smaller than 0.5 mm or the chemical assay tape has a nonfibrous porous layer, it is preferable that the diameter of the roll be 40 mm or more.

Preferably, a leader is attached to an (outer) end of the assay tape which has been wound up. The length of the leader is preferably at least 3.2 times that of the diameter of the roll. Another guide tape may be attached to the other (inner) end of the assay tape which is wound up.

When the chemical assay tape has a width such that the liquid sample spreads substantially uniformly in all directions on the film surface, the amount of the liquid sample spotted onto the assay tape is proportional to the area over which the liquid sample spreads. On the other hand, for economy's sake, the width of the chemical assay tape should be as narrow as possible, since the liquid sample usually spreads into only a part of the chemical assay tape where a detectable change in color or the like is produced. When the width of the chemical assay tape is smaller than the radius of the area over which the liquid sample freely spreads, the spreading of the liquid sample is restricted in the transverse direction of the chemical assay tape. A proportional relationship still exists between the amount of the liquid sample and the area over which the liquid sample spreads, as long as the volume of the liquid sample $S(\mu l)$ satisfies the following condition:

$\frac{1}{4}(\pi h P w^2) < S < 3/2(\pi h p W^2)$ wherein W represents the width of the chemical assay tape (mm), h represents the thickness of the spreading layer (mm), and P represents the porosity

EXAMPLE

A multilayer chemical assay tape for determining the amount of creatinine was prepared in the following manner:

On a transparent polyethylene terephthalate (PET) film (having a thickness of 180 $\mu$m), an indicator layer was applied with the proportions of the respective constituents indicated below. After drying, a polypropylene membrane filter (having an average pore size of 0.2 $\mu$m, a porosity of 75% and a thickness of 170 $\mu$m), is uniformly attached thereto by pressure so as to form a gas-transmissive barrier layer.

| Indicator Layer | |
|---|---|
| | amount/m² |
| Bromophenol Blue | 340 mg |
| Polyvinyl acetate-ethyl acrylate copolymer latex | 8.5 g |
| N-polyoxyethylene-N-octane sulfonamide (average degree of ethoxy unit polymerization: 16) | 100 mg |

Then, on the barrier layer, a reaction layer, an intermediate layer and an endogenous ammonium trapping layer were successively applied as aqueous solutions with the coating amounts of the respective constituents indicated below and dried.

| | amount/m² |
|---|---|
| Reaction Layer | |
| alkali-treated gelatin | 11.7 g |
| sodium tetraborate | 1.7 g |
| p-nonylphenoxypolyglycidol (average glycidol unit: 10) | 0.3 g |
| creatinine iminohydrase (EC 3.5.4.21) | 750 units |
| Intermediate Layer | |
| alkali-treated gelatin | 16.6 g |
| p-nonylphenoxypolyglycidol (average glycidol unit: 10) | 0.2 g |
| sodium tetraborate | 0.75 g |
| pH of coating solution: 9.0 | |
| thickness after drying: 7.5 μm | |
| Endogenous Ammonium Trapping Layer | |
| alkali-treated gelatin | 7.5 g |
| sodium tetraborate | 1.35 g |
| p-nonylphenoxypolyglycidol (average glycidol unit: 10) | 0.17 g |
| α-ketoglutaric acid | 2.5 g |
| NADPH | 1.6 g |
| glutamic acid dehydrogenase (EC 1.4.1.4) | 70000 units |
| pH of coating solution 8.0 | |

The endogenous ammonium trapping layer was substantially uniformly swelled with a 0.2% p-nonylphenoxypolyglycidol aqueous solution. Immediately thereafter, polyester knitted material which had been subjected to glow discharge processing (which had a gauge number of 40 and the amount of which had been reduced by 25% by means of NaOH) was brought into contact with the endogenous ammonium trapping layer. They were passed through pressing rollers so that they were uniformly laminated together.

Further, an aqueous composition with the proportions of the respective constituents indicated below was applied to the knitted material so that the knitted material was impregnated with the aqueous composition. Then it was dried to form a spreading layer.

| Spreading Layer | |
|---|---|
| | amount/m² |
| methylcellulose (viscosity of 2% aqueous solution at 20° C.: 50 cps) | 800 mg |
| hydroxypropylmethylcellulose (containing 28-30% methoxy group and 7-12% hydroxypropoxy group; viscosity of 2% aqueous solution at 20° C.: 50 cps) | 800 mg |
| titanium dioxide fine particles (rutile type; particle size 0.25-0.40 μm) | 10.7 g |
| nonylphenoxypolyethoxyethanol (average degree of ethoxy unit polymerization: 40) | 2.0 g |
| p-nonylphenoxypolyglycidol (average glycidol unit: 10) | 220 mg |

The film thus formed was cut into tapes having a width of 5 mm and a length of 1 m. Through all the layers of these tapes except the support layers, grooves were provided across the width of the tape with intervals of 10 mm, 30 mm and 100 mm, respectively. A tape without grooves was also prepared. Then, each tape was wound up around a core having a diameter of 60 mm such that the spreading layer was on the exterior surface.

After each wound tape had been dried in a vacuum at 2 mmHg for 48 hours, the film surface was observed. The results are shown in the following Table.

TABLE

| interval between grooves | crack |
|---|---|
| 10 mm | none |
| 30 mm | none |
| 100 mm | detected |
| ∞ (no groove) | detected |

From these results, it is clear that the chemical assay tape having grooves in accordance with the present invention does not crack easily even after vacuum drying. Results similar to those shown in Table were obtained when the tape was wound up such that the spreading layer was on the inner surface.

I claim:

1. In a chemical assay tape for determining the amount of a substance contained in a liquid sample, said tape comprising a water-impermeable support, at least one water permeable porous spreading layer and at least one water permeable porous reagent layer which is disposed between said support and said at least one porous spreading layer, one of said at least one reagent layer having reagent material therein and one of said at least one spreading layer being positioned farthest from said support so as to form a radially outermost layer of said tape upon winding of said tape, the improvement comprising means for preventing the formation of minute stress cracks in said radially outermost layer of said tape attendant to the winding and storage thereof on a reel, said preventing means comprising a plurality of stress relieving grooves which are spaced at substantially constant intervals, said grooves extending perpendicular to a length of said chemical assay tape, wherein said plurality of grooves are spaced from each other by a distance sufficient to prevent cracking of said radially outermost layer, said grooves extending at least through said radially outermost layer but through fewer than all of said reagent and spreading layers.

2. A chemical assay tape as defined in claim 1 in which each of said at least one spreading layer is a fibrous porous layer.

3. A chemical assay tape as defined in claim 1 in which said constant interval is less than 50 mm.

4. A chemical assay tape as defined in claim 1 in which said constant interval is at most 30 mm.

5. The chemical assay tape as in claim 1 wherein said grooves only extend through said porous spreading layer which is farthest from the support.

6. The chemical assay tape as in claim 1 further comprising a filter layer positioned between said porous spreading layer which is farthest from said support and said at least one reagent layer wherein said grooves only extend through said porous spreading layer which is farthest from said support through said filter layer.

7. The chemical assay tape as in claim 1 wherein said grooves extend through said porous spreading layer which is farthest from said support and one of said at least one reagent layer.

* * * * *